United States Patent
Ruff (10) Patent No.: US 9,983,214 B2
(45) Date of Patent: May 29, 2018

(54) METHOD FOR EVALUATING ARTICULAR JOINT THERAPEUTICS

(71) Applicant: ESM TECHNOLOGIES, LLC, Carthage, MO (US)

(72) Inventor: Kevin J. Ruff, Carthage, MO (US)

(73) Assignee: ESM Technologies, LLC, Carthage, MO (US)

( * ) Notice: Subject to any disclaimer, the term of this patent is extended or adjusted under 35 U.S.C. 154(b) by 42 days.

(21) Appl. No.: 15/130,120

(22) Filed: Apr. 15, 2016

(65) Prior Publication Data

US 2017/0299611 A1    Oct. 19, 2017

(51) Int. Cl.
*G01N 33/53* (2006.01)
*G01N 33/68* (2006.01)
*A61K 35/57* (2015.01)

(52) U.S. Cl.
CPC ......... *G01N 33/6887* (2013.01); *A61K 35/57* (2013.01); *G01N 2333/78* (2013.01); *G01N 2800/10* (2013.01); *G01N 2800/52* (2013.01)

(58) Field of Classification Search
None
See application file for complete search history.

(56) References Cited

PUBLICATIONS

Henrotin et al. Complementary and Alternative Medicine 2014 vol. 14, p. 159 (total 7 pages) Tiraloche et al. Arthritis & Rheumatism 2005 vol. 52, p. 1118-1128.*
Kraus et al. (Arthritis Research Conference 1997 sponsored by AF, NIAMS, ACR; Abstract only).*
Petersen et al. (Osteoarthritis and cartilage 2010 vol. 18, p. 34-40).*

* cited by examiner

*Primary Examiner* — Changhwa J Cheu
(74) *Attorney, Agent, or Firm* — Hoffman Baron, LLP (57) ABSTRACT

The invention provides a method for determining the efficacy of compositions used to treat articular joint conditions in mammals. The method includes measuring the change in levels of one or more cartilage degradation biomarkers in a mammal from before exercise and after exercise, then administering a composition used to treat articular joint conditions to the mammal, and measuring the change in levels of one or more cartilage degradation biomarkers in the mammal from before exercise and after exercise.

30 Claims, 2 Drawing Sheets

METHOD FOR EVALUATING ARTICULAR JOINT THERAPEUTICS

FIELD OF THE INVENTION

The present invention relates to methods for evaluating articular joint therapeutics in either healthy or diseased individuals.

BACKGROUND OF THE INVENTION

Estimates by the World Health Organization of the global prevalence of the top two articular joint diseases in people put the incidence of osteoarthritis (OA) in adults over 60 years of age at 9.6% of men and 18.0% of women (approximately 84 million people combined) and the incidence of rheumatoid arthritis (RA) in adults 25 years and older at 1% (approximately 42 million people). These rates of incidence are expected to increase nearly exponentially as the global population ages.

Both OA & RA share the same basic disease pathology in that the articular joints become inflamed, which leads to destruction of the cartilage that normally would cushion the joint. The inflammation and subsequent cartilage loss leads to joint stiffness and pain, at which point people begin looking for pharmacologic interventions to treat these symptoms. At this stage, the patients have likely had joint inflammation for many years, with cartilage destruction occurring asymptomatically the entire time. This makes the condition that much more difficult to treat. The lack of drugs that can halt the progression of arthritis (i.e be disease modifying) combined with the fact that it is diagnosed when it is more severe, results in OA & RA being a substantial burden for global healthcare systems. Because so many people acquire these debilitating diseases, there is an obvious current need for joint therapeutics and the future need will be substantially greater.

There are currently no approved disease modifying osteoarthritis drugs (DMOADs) and only a handful of disease modifying anti-rheumatic drugs (DMARDs) are approved, such as antibodies—with the latter having severe side effects, some of which can even be fatal. The ability to evaluate new joint therapeutics is paramount to the approval of new molecular entities or for new indications for existing drugs.

Various indicators of disease status (biomarkers) have been evaluated to better understand arthritis progression and/or prognosis and to better guide the development of therapeutic interventions. Researchers have looked at immune cell patterns in the joints, serological parameters (e.g. cholesterol & triglycerides) and markers of oxidative stress (e.g malondialdehyde & C-reactive protein (CRP), synovial fluid cytokine levels (e.g. TNF-α, IL-1β, IL-6, etc.), as well as cartilage components in synovial fluid (e.g. chondroitin sulfate, glycosaminoglycans, hyaluronic acid, etc.). Many of these biomarkers suffer from a number of drawbacks, from lack of specificity (e.g. cholesterol) to difficulty in obtaining samples (e.g. synovial fluid). Because of the plethora of biomarkers from which to choose to evaluate arthritis, the Osteoarthritis Biomarkers Network funded by the National Institutes of Health/National Institute of Arthritis, Musculoskeletal, and Skin Disease (NIH/NIAMS) proposed a classification scheme for biomarkers to provide a common format for communication of research in this area. This scheme is termed BIPED which is an acronym for Burden of disease, Investigative, Prognostic, Efficacy of intervention, and Diagnostic. These characteristics help to rank biomarkers as to their clinical utility in diagnosing and treating arthritis. Based upon these criteria, indicators of cartilage metabolism (i.e. synthesis and degradation) have moved to the top of the list of biomarker candidates likely to be most useful.

Cartilage is primarily composed of extracellular matrix (ECM), a composite network of proteins such as type-II collagen interacting with negatively charged polysaccharides such as hyaluronic acid and chondroitin sulfate, all of which are synthesized and secreted by the cells of cartilage known as chondrocytes. During normal cartilage turnover (metabolism) in healthy articular joints, ECM production balances ECM breakdown, thereby ensuring the continuous renewal of this critical joint-cushioning tissue. However under pathological (disease) conditions, ECM synthesis cannot keep pace with degradation and a loss of the structural integrity of the articular cartilage results. Products of this degradation imbalance can be found in both blood and urine of arthritic patients.

A number of these biomarkers of cartilage turnover (i.e. degradation & synthesis) have been investigated for their diagnostic and prognostic properties. Two of the most widely studied cartilage degradation biomarkers are c-terminal cross-linked telopeptide of type-II collagen (CTX-II) and cartilage oligomeric matrix protein (COMP). Two of the most widely studied cartilage synthesis biomarkers are procollagen type-IIA N-terminal propeptide (PIIANP) and carboxypeptide of procollagen type-II (CPII). Of all of the cartilage turnover biomarkers, urinary CTX-II has shown the most diagnostic and prognostic potential according to the BIPED system.

CTX-II has been associated with both the incidence and progression of osteoarthritis (OA) in multiple clinical trials and is predictive of the progression of OA both radiographically, including two 5+ year longitudinal studies, and by magnetic resonance imaging. Urinary CTX-II levels are known to be substantially elevated in the subset of the population with articular joint disease (i.e. OA & RA), but levels are also known to be elevated in a variety of healthy subsets of the population, as well.

For example, urinary CTX-II levels in growing children are about 50-fold higher than that of adults. Urinary CTX-II levels have been shown to be elevated due to high-impact, strenuous exercise in healthy college-aged endurance athletes such as cross-country runners by about 85% over age- and weight-matched controls, but were not significantly elevated in lower-impact endurance athletes like swimmers and rowers. Urinary CTX-II has also been shown to be about 2-fold higher in post-menopausal women versus age-matched pre-menopausal women and moderately elevated (~25%) in overweight people (BMI ≥25 kg/m$^2$) versus normal-weight controls (BMI <25 kg/m$^2$).

SUMMARY OF THE INVENTION

The invention provides a method for determining the efficacy of compositions used to treat articular joint conditions in mammals. The method includes measuring the change in levels of one or more cartilage degradation biomarkers in a mammal from before exercise and after exercise, then administering a composition used to treat articular joint conditions to the mammal, and measuring the change in levels of one or more cartilage degradation biomarkers in the mammal from before exercise and after exercise.

According to the invention, a decrease in the change in levels of cartilage degradation biomarkers after exercise (but before administration of a composition used to treat articular joint conditions) as compared to the level of said biomarkers after exercise (and after administration of a composition used to treat articular joint conditions) indicates that the composition is effective to treat articular joint conditions in said mammal.

In another embodiment, a method for determining the efficacy of compositions used to treat articular joint conditions in mammals is provided. The method includes administering a composition used to treat articular joint conditions to all but one group of two or more groups of mammals, and subsequently measuring the change in levels of one or more cartilage degradation biomarkers in the groups of mammals from before exercise and after exercise. In this embodiment, a decrease in the change in levels of cartilage degradation biomarkers after exercise in the group or groups to which the compound was administered as compared to the level of said biomarkers after exercise in the group to which the composition was not administered (untreated) indicates that the composition is effective to treat articular joint conditions in said mammal.

In an embodiment of the invention, one or more cartilage degradation biomarkers is selected from the group consisting of c-terminal cross-linked telopeptide of type-I collagen (CTX-I), c-terminal cross-linked telopeptide of type-II collagen (CTX-II), N-terminal cross-linked telopeptide of type-I collagen (NTX-I), cartilage oligomeric matrix protein (COMP), glycosaminoglycans, type-II collagen neoepitope (TIINE), collagen type-II cleavage product (C2C), collagen type-II-specific neoepitope (C2M), 9-amino acid peptide of type-II collagen and its nitrated form (Coll 2-1 & Coll 2-1-$NO_2$), fibulin 3 peptides (Fib3-1 & Fib3-2), follistatin-like protein 1 (FSTL-1), cartilage glycoprotein 39 (YKL-40), type-I and type-II collagen cleavage neoepitopes (C1 & C2), pyridinoline (PYR), glucosyl-galactosyl-pyridinoline (Glc-Gal-PYR), and helical peptide of type-II collagen (HE-LIX-II).

In another aspect, one or more cartilage synthesis biomarkers is selected from the group consisting of procollagen type-IIA N-terminal propeptide (PIIANP), carboxypeptide of procollagen type-II (CPII) or C-terminal propeptide of type-II procollagen (PIICP), and chondroitin sulfate epitope 846 from aggrecan (CS846).

According to the invention, the cartilage degradation and synthesis biomarkers are obtained from synovial fluid, whole blood, serum, or urine of said mammal, and the articular joint is selected from, for example, spine, shoulders, elbows, wrists, fingers, hips, knees, ankles, and toes.

In one embodiment, the exercise is of low impact to the articular joint and of moderate intensity. The low impact exercise is selected from, for example, walking, roller skating, swimming, cycling, yoga, rowing, water aerobics, stair climbing, and weight lifting.

In a preferred embodiment, the exercise is performed for a brief period per day for a number of weeks. In accordance with the invention, the mammal is suffering from an articular joint disease. In one aspect, the articular joint disease is selected from the group consisting of osteoarthritis, rheumatoid arthritis, psoriatic arthritis, juvenile arthritis, ankylosing spondylitis, gout, gouty arthritis, tendinitis, synovitis, Sjögren's Syndrome, septic arthritis, or systemic lupus erythematosis.

In another embodiment, the mammal is pre-diseased, or is completely asymptomatic, but has underlying detrimental articular joint structural changes. In a preferred embodiment the pre-diseased, or completely asymptomatic mammal that has underlying detrimental articular joint structural changes is obese or a post-menopausal female, or both.

In a further embodiment, the mammal is healthy and does not experience any articular joint disease symptoms nor has any underlying detrimental articular joint structural changes. In a preferred embodiment, the mammal that is healthy and does not experience any articular joint disease symptoms nor has any underlying detrimental articular joint structural changes is obese or a post-menopausal female, or both.

In one aspect, the composition is a chondroprotective agent, and is selected from, for example, glucosamine; glycosaminoglycans; methylsulfonylmethane (MSM); S-adenosylmethionine (SAMe); eggshell membrane or eggshell membrane hydrolyzates; an omega-3 or omega-6 polyunsaturated fatty acid; *Boswellia* species or *Boswellia* extract; turmeric or turmeric extract; curcumin or curcuminoids; white willow bark or white willow bark extract; proteolytic enzymes; collagen or collagen hydrolyzates; pine bark extract; cetylated fatty acids; plant extracts; a vitamin or vitamin pre-cursor; a mineral, or combinations thereof.

In another aspect, the composition affects or is intended to affect joint-related symptomology. In one embodiment, the joint-related symptomology is, for example, pain; burning; aching; tenderness; discomfort; stiffness; swelling; localized fever or warmth; inflexibility; limitation in or decreased range of motion; crepitus; partial loss of function; loss of weight-bearing capacity or weakness; or combinations thereof.

In a final embodiment, the joint-related symptomology is evaluated during or immediately after exercise or some time period following exercise, or a combination thereof.

DETAILED DESCRIPTION OF THE INVENTION

The present invention relates to a method to rapidly and systematically evaluate articular joint therapeutic compositions in either diseased or healthy individuals. The invention provides a method for determining the efficacy of compositions used to treat articular joint conditions in mammals. By "efficacy," it is meant that the compositions are effective to reduce levels of cartilage degradation biomarkers in a mammal.

The method includes measuring the change in levels of one or more cartilage degradation biomarkers in a mammal from before exercise and after exercise, then administering a composition used to treat articular joint conditions to the mammal, and measuring the change in levels of one or more cartilage degradation biomarkers in the mammal from before exercise and after exercise.

According to the invention, a decrease in the change in levels of cartilage degradation biomarkers after exercise (but before administration of a composition used to treat articular joint conditions) as compared to the level of said biomarkers after exercise (and after administration of a composition used to treat articular joint conditions) indicates that the composition is effective to treat articular joint conditions in said mammal.

The invention also provides an alternative method that includes administering a composition used to treat articular joint conditions to all but one group of two or more groups of mammals, and subsequently measuring the change in levels of one or more cartilage degradation biomarkers in the groups of mammals from before exercise and after exercise. In this embodiment, a decrease in the change in levels of cartilage degradation biomarkers after exercise in the group or groups to which the compound was administered as compared to the level of said biomarkers after exercise in the group to which the composition was not administered (untreated) indicates that the composition is effective to treat articular joint conditions in said mammal.

In measuring the change in levels of biomarkers, a greater percentage of decrease in biomarker correlates with a greater efficacy of the compound administered. However, any decrease in the level of biomarker translates to effectiveness of the compound.

Use of the terminology 'composition used to treat articular joint conditions' or its plural is intended for the purposes of the present invention to mean any composition or agent administered to a subject that confers a therapeutic effect in any articular joint of said subject. Examples of such compositions include, but are not limited to, chondroprotective agents, for example, glucosamine; glycosaminoglycans; methylsulfonylmethane (MSM); S-adenosylmethionine (SAMe); eggshell membrane or eggshell membrane hydrolysates; an omega-3 or omega-6 polyunsaturated fatty acid; *Boswellia* species or *Boswellia* extract; turmeric or turmeric extract; curcumin or curcuminoids; white willow bark or white willow bark extract; proteolytic enzymes; collagen or collagen hydrolyzates; pine bark extract; cetylated fatty acids; plant extracts; a vitamin or vitamin pre-cursor; a mineral, or combinations thereof.

In addition to the above compositions, any pharmaceutical composition that is known to be effective in treating articular joint conditions is contemplated for the invention. For example, compositions include acetaminophen, diclofenac, ibuprofen, celecoxib, propoxyphene, or any other analgesics, non-steroidal anti-inflammatory drugs (NSAIDs), or narcotics, or combinations thereof.

According to the invention, articular joint conditions includes, for example, osteoarthritis, rheumatoid arthritis, psoriatic arthritis, juvenile arthritis, ankylosing spondylitis, gout, gouty arthritis, tendinitis, synovitis, Sjögren's Syndrome, septic arthritis, or systemic lupus erythematosis.

The therapeutic compositions are administered topically, orally, or by injection to the subject.

"Mammals" includes any mammal. Preferably, the mammal is a human. The mammal can also be a domesticated animal or a farm animal. Examples of domestic animals includes, for example, dogs, cats and rabbits. Examples of farm animals includes, for example, horses, cows and pigs.

"Cartilage degradation biomarkers" includes many different types of fragments that are produced when cartilage degradation occurs through biological processes. These fragmentation products can be found in the synovial fluid, whole blood, serum, and urine of subjects experiencing cartilage degradation. Examples of these include, for example, c-terminal cross-linked telopeptide of type-I collagen (CTX-I), c-terminal cross-linked telopeptide of type-II collagen (CTX-II), N-terminal cross-linked telopeptide of type-I collagen (NTX-I), cartilage oligomeric matrix protein (COMP), glycosaminoglycans (e.g. keratan sulfate, dermatan sulfate, chondroitin sulfate, hyaluronic acid, etc.), type-II collagen neoepitope (TIINE), collagen type-II cleavage product (C2C), collagen type-II-specific neoepitope (C2M), 9-amino acid peptide of type-II collagen and its nitrated form (Coll 2-1 & Coll 2-1-$NO_2$), fibulin 3 peptides (Fib3-1 & Fib3-2), follistatin-like protein 1 (FSTL-1), cartilage glycoprotein 39 (YKL-40), type-I and type-II collagen cleavage neoepitopes (C1 & C2), pyridinoline (PYR), glucosyl-galactosyl-pyridinoline (Glc-Gal-PYR), and helical peptide of type-II collagen (HELIX-II).

The biomarker can also be a cartilage synthesis biomarker such as PIIANP or CPII. There are a number of pro-collagen and other protein fragments known to be necessary to synthesize and/or repair cartilage. These synthetic fragments can be found in the synovial fluid, serum, and urine of subjects experiencing cartilage synthesis or repair. Examples of these are: procollagen type-IIA N-terminal propeptide (PIIANP), carboxypeptide of procollagen type-II (CPII) or C-terminal propeptide of type-II procollagen (PIICP), and chondroitin sulfate epitope 846 from aggrecan (CS846).

In yet another aspect of the invention, the ratio of a cartilage degradation biomarker to a cartilage synthesis biomarker can be employed. Cartilage turnover or cartilage metabolism is the balance within an organism of cartilage degradation and cartilage synthesis or repair. The ratio of these two types of biomarkers can sometimes be a better indicator of overall articular cartilage health status than either type of biomarker separately. Examples of cartilage turnover ratios are: CTX-II/CPII, COMP/PIIANP, CTX-II/PIIANP, and COMP/CPII.

Use of the term 'biomarker' or its plural is intended to mean a characteristic or characteristics that are objectively measured and evaluated as indicators of normal biological processes, pathogenic (disease) processes, or pharmacologic responses to therapeutic interventions.

Exercise: According to the invention, subjects perform a low-impact, moderate intensity exercise such as climbing stairs or lifting weights for a brief period per day on alternating days for a number of consecutive weeks. At the end of each week, subjects provide urine and blood samples from which biomarker levels can be obtained that can be compared to baseline (pre-exercise) values. Traditional joint therapeutic clinical trial designs have a duration of 3-6 months for 'short-term' studies and 1-5 years for 'long-term' studies.

This is because of the perceived long time frame required to observe biological changes related to articular joint disease. This includes changes in symptoms (i.e. pain, stiffness, functional loss, etc.) as well as changes in objective indicators of disease progression (i.e. biomarkers, joint space width, etc.). The unexpected, short-term increase in cartilage biomarker levels from low-impact, moderate intensity exercise allows for the objective evaluation of chondroprotective (cartilage-sparing) joint therapeutics in as little as 24 hours to 2-4 weeks. Thus the invention leads to a 6-fold or greater reduction in study duration versus prior art (i.e. 2 weeks versus 12 weeks). One of ordinary skill in the art can envision the use of alternative study durations (e.g. 4 weeks, 6 weeks, 8 weeks, etc.) or the application of the invention study design in alternative formats. For example, having subjects exercise every day instead of alternating days or having subjects exercise on alternating days for 2 weeks followed by a period of inactivity (e.g. 2 months, 6 months, 12 months, etc.) and then another subsequent period of exercise on alternating days for 2 weeks in order to compare the response of the subjects articular joints to the exercise regimen over longer time periods. Such equivalents and alternatives are intended to be encompassed in the scope of the present invention.

Use of the term 'low-impact' is intended to mean exercises during which there are minimal axial forces experienced by the articular joints. Often with these types of exercises, one foot remains on the ground at all times and there are no jarring motions (e.g. as from jumping, hopping, skipping, running, etc.). Another aspect of these types of exercises can be where water or a machine or device supports part or all of the body while exercising. Examples of low-impact exercises include but are not limited to: walking (flat surface, inclined treadmill, etc.), roller skating, swimming, cycling, yoga, rowing, water aerobics, stair climbing, and some forms of weight lifting.

Use of the term 'moderate' is intended to mean exercises that do not require high levels of exertion or intense movements and during which the subject's heart rate does not increase substantially (i.e. more than 20-30%). For example, walking $1/4^{th}$ of a mile in 10 minutes versus walking the same distance in only 5 minutes would be a moderate walking pace. Other examples would be climbing 5 flights of stairs in 10 minutes versus climbing them in only 5 minutes, or swimming 5 laps in a pool in 10 minutes versus swimming them in only 5 minutes. These non-limiting examples are provided for clarification of the terminology and are not intended to encompass the entire scope of the present invention.

The method of the invention is directed to the evaluation of articular joints, which includes but is not limited to: spine (including neck and back), shoulders, elbows, wrists, fingers, hips, knees, ankles, and toes. More preferably, the invention is directed to large articular joints such as shoulders, hips, elbows and knees. The low-impact, moderate intensity exercise performed in the invention would have to be chosen such that it results in articulation (motion) of the particular articular joint being evaluated. For example, climbing stairs would primarily affect the knees, whereas lifting weights above the head would primarily affect the shoulders. These non-limiting examples are provided for clarification and are not intended to encompass the entire scope of the present invention.

In one aspect of the invention, the method can be employed with individuals suffering from articular joint diseases including a wide variety of arthropathies. Examples of articular joint diseases include but are not limited to: osteoarthritis, rheumatoid arthritis, psoriatic arthritis, juvenile arthritis, ankylosing spondylitis, gout, gouty arthritis, tendinitis, synovitis, Sjögren's Syndrome, septic (or infectious) arthritis, or systemic lupus erythematosis.

In another aspect of the invention, the method can be employed with pre-diseased individuals, in which articular joint disease is present but is asymptomatic. A pre-diseased state is one in which articular cartilage damage may be occurring, but there are no or insufficient clinical symptoms of disease which could afford a diagnosis of such disease, and the subject's joints would otherwise be considered healthy. Biomarkers used to measure the status of this pre-diseased state are only slightly outside the norm that results from natural variation within subjects of the same gender, age, and weight, but are not sufficiently abnormal to qualify as a diseased condition. This would generally be in a range of plus or minus 10-20% from the mean or norm for measurable biomarkers. The inventors believe that the joints of these subjects would be substantially more sensitive to exercise-induced cartilage turnover. Although the subject is considered healthy, they may experience periodic instances of joint disease symptoms (i.e. pain, stiffness, functional loss, etc.) and they would benefit from the administration of a therapeutic intervention; and such treatment could even possibly prevent the subject from reaching a fully symptomatic diseased state.

Use of the term 'periodic' is intended to mean a condition that recurs from time to time, but not consistently or chronically. Thus the condition could occur one or several days per week, but not every day. More preferably, the condition occurs less frequently, such as one or several days per month.

In yet another aspect of the invention, the method can be employed with healthy individuals, in which no articular joint disease is present. Biomarkers used to measure the status of healthy joints would be well within the norm that results from natural variation within subjects of the same gender, age, and weight, and these subjects would have no clinical signs or symptoms of articular joint disease (See Table 1 for expected CTX-II ranges).

TABLE 1

Expected ranges for urinary CTX-II for various age groups

| | Women | Men |
|---|---|---|
| Age | | |
| 20-25 | 450-550 | 300-400 |
| 30-50 | 100-150 | 100-150 |
| >50 | — | 150-250 |
| Pre-menopausal | 100-150 | N/A |
| Post- | 200-300 | N/A |
| Radiographic OA ≥35 | 250-450 | |
| BMI <25 kg/m$^2$ | 100-150 | |
| BMI ≥25 kg/m$^2$ | 150-200 | |
| Radiographic | 450-550 | 250-350 |

Values are reported as nanograms of CTX-II corrected for millimoles of creatinine (ng/mmol Cr).

There are a number of special sub-groups of healthy individuals whose joint cartilage has been found by the inventors to be un-expectedly sensitive to turnover induced by exercise. These groups are post-menopausal women (see Examples 1-3) and overweight individuals (either gender) (see Example 4). Without being bound by theory, the inventors believe that biochemical changes occur in the joints of post-menopausal women and overweight individuals that make their cartilage particularly susceptible to damage, especially over long periods of time. This is likely why these sub-groups of individuals have a significantly higher likelihood of developing articular joint disease in their lifetimes.

Because the cartilage turnover is exercise-induced, there is also a concomitant increase in joint discomfort (i.e. pain, stiffness, etc.) allowing for the subjective evaluation of joint-related symptom therapeutics (those that would reduce joint pain, stiffness, etc.), as well. In another aspect of the invention, subjects complete a survey or questionnaire that asks them to grade their subjective joint-related symptoms. This could include evaluation during or immediately after exercise or some time period following exercise, such as 6, 12, 24 or 48 hours post-exercise. Examples of subjective joint-related symptoms include, but are not limited to: pain, burning, aching, tenderness, discomfort, stiffness (i.e. temporary as in the morning, or persistent), swelling, localized fever or warmth, inflexibility, limitation in or decreased range of motion, crepitus (i.e. grating, crackling, or popping sounds or sensations in the joint), partial loss of function (e.g. difficulty in getting up from a seated position, difficulty in getting in and out of a vehicle, difficulty in climbing stairs, etc.), and loss of weight-bearing capacity or weakness. All of these symptoms can be temporary, intermittent or periodic, or chronic.

In another aspect of the invention, the articular joint therapeutic can be evaluated in a variety of clinical trial designs, including but not limited to: open-label, single-blind, double-blind, placebo-controlled, active comparator, superiority, non-inferiority, or any combinations or variations thereof. The use of the term 'open-label' is intended to mean a trial in which an investigational therapeutic is evaluated without a comparator (i.e. placebo or active) and the study subject(s) and investigator(s) are aware of the identity of the therapeutic. The use of the term 'single-blind' is intended to mean a trial in which either the subject(s) or the investigator(s) are unaware of treatment assignment (i.e. whether the subjects are receiving the investigational therapeutic or a placebo or active comparator); most commonly this term is used to describe the subject(s) being unaware of treatment assignment. The use of the term 'double-blind' is intended to mean a trial in which both the subject(s) and the investigator(s) are unaware of treatment assignment (i.e. whether the subjects are receiving the investigational therapeutic or a placebo or active comparator). The use of the term 'placebo-controlled' is intended to mean a trial in which the investigational therapeutic is being compared to a placebo (i.e. a dosage form that lacks an active therapeutic ingredient but is indistinguishable from the dosage form that does contain an active therapeutic); A placebo is commonly referred to as a sugar pill. The use of the term 'active comparator' is intended to mean a trial in which an investigational therapeutic is being compared to another non-investigational active therapeutic intended for the same or a similar therapeutic purpose. The use of the term 'superiority' is intended to mean a trial in which the investigational therapeutic must be superior to or better than a comparator (i.e. placebo or active) in order to have been deemed a success. The use of the term 'non-inferiority' is intended to mean a trial in which the investigational therapeutic must not be inferior to or worse than a comparator (i.e. placebo or active) in order to have been deemed a success. One of ordinary skill in the art can easily envision modifications to the abovementioned study designs or the use of alternative study designs. Such equivalents and alternatives are intended to be encompassed in the scope of the present invention.

Thus, in a preferred embodiment, a chondroprotective joint therapeutic composition would be evaluated in an open-label clinical trial design. Wherein: subjects would serve as their own control group by first performing a low-impact, moderately intense exercise that works the knees (e.g. inclined treadmill, seated step machine with resistance, climbing stairs, seated leg press to lift weights, etc.) for up to 10 minutes per day on alternating days for 2 consecutive weeks; during the two-week study period, subjects would be asked to complete a post-exercise questionnaire wherein they rate any knee pain or stiffness during or immediately (up to 1 hour) after exercise and then again rate any knee pain or stiffness approximately 12 hours post-exercise (e.g. the next morning); at the end of each week, subjects provide urine and blood samples from which biomarker levels would be obtained. There would then be a resting period of 2 weeks or more to allow the subject's knees to return to their basal state. The same exercise regimen would be repeated (i.e. 10 minutes per day, alternating days for 2 weeks), with the subjects being aware that they are consuming a chondroprotective joint therapeutic composition. The subjects would once again complete post-exercise questionnaires for knee pain and stiffness and would provide blood and urine samples weekly for biomarker analysis. Once all of these study procedures were completed, the biomarker levels and pain and stiffness levels from the treatment period (i.e. $2^{nd}$ exercise period) would be compared to the biomarker levels and pain and stiffness levels from the control period (i.e. $1^{st}$ exercise period) to determine whether the chondroprotective therapeutic reduced the amount of cartilage turnover induced by the exercise regimen (i.e. a lesser increase in a cartilage degradation biomarker) and/or whether the joint therapeutic composition reduced associated knee pain or stiffness.

In a more preferred embodiment, a chondroprotective joint therapeutic composition would be evaluated in a randomized, double-blind, placebo-controlled clinical trial design. Wherein: subjects would be randomized (similar to the flip of a coin or the roll of dice) to either an investigational therapeutic or placebo group in a double-blind fashion; subjects in both groups would then perform a low-impact, moderately intense exercise that works the knees (e.g. inclined treadmill, seated step machine with resistance, climbing stairs, seated leg press to lift weight, etc.) for up to 10 minutes per day on alternating days for 2 consecutive weeks; during the two-week study period, subjects would be asked to complete a post-exercise questionnaire wherein they rate any knee pain or stiffness during or immediately (up to 1 hour) after exercise and then again rate any knee pain or stiffness approximately 12 hours post-exercise (e.g. the next morning); at the end of each week, subjects provide urine and blood samples from which biomarker levels would be obtained. Once the study procedures were completed, the treatment group assignment would be un-blinded and biomarker levels and pain and stiffness levels would be compared between the two groups (i.e. investigational therapeutic versus placebo) to determine whether the chondroprotective joint therapeutic composition reduced the amount of cartilage turnover induced by the exercise regimen (i.e. a lesser increase in a cartilage degradation biomarker) and/or whether the therapeutic reduced associated knee pain or stiffness.

Although the present invention is directed to humans, one of ordinary skill in the art could envision the use of the same or a similar study design in other mammals, such as dogs, cats, rabbits, horses, cows, goats, pigs, etc. Furthermore, in some examples the present application has been described with reference to only a limited number of low-impact, moderate intensity exercises by which cartilage turnover is induced. One skilled in the art can easily ascertain various exercise methods that would induce cartilage turnover, such as by increasing intensity of the exercise or by increasing the extent of impact the joints sustain (i.e. high-impact exercise) or by increasing the frequency of exercise. All such equivalents or alternatives are intended to be encompassed in the scope of the present invention.

The invention also relates to a personal test kit that can be employed by an individual or in a clinical setting. The test kit includes a means for collecting a sample from the individual, and the means for testing the sample for the one or more cartilage degradation and/or synthesis biomarkers. Means for quantification of the one or more cartilage degradation and/or synthesis biomarkers is also present in the kit. Such a kit would allow an individual to assess his or her cartilage degradation and/or synthesis pre and post workout, and in addition evaluate any supplements (i.e. compositions, pharmaceuticals, etc) that are being consumed for their effect on cartilage degradation and/or synthesis.

The sample collected for use with the kit can be urine, blood or saliva. The means for testing the sample for said one or more cartilage degradation and/or synthesis biomarkers is any suitable assay, including for example, enzyme-linked immunosorbent assay (ELISA).

EXAMPLES

The following non-limiting examples have been carried out to illustrate various embodiments of the invention:

Example 1

Determination of the Temporal Urinary Clearance of the Cartilage Degradation Biomarker CTX-II in Both Healthy and Arthritic Humans Over 24 Hours The following example is illustrative of the determination of the temporal urinary clearance of the cartilage degradation biomarker CTX-II in both healthy and arthritic humans over 24 hours. Proteins in the bloodstream are known to be cleared over time by the human body via excretion in urine by the kidneys. This protein clearance occurs at different rates for different individuals and so an internal protein standard that is always present in urine, such as creatinine, is frequently used to normalize the clearance rates so that they can be compared between individuals or groups of individuals. Thus the ratio of urinary CTX-II, expressed in nanograms per deciliter (ng/dL), to urinary creatinine (Cr), expressed in millimoles per deciliter (mmol/dL) is calculated and the results are reported as nanograms of CTX-II per millimole of creatinine (ng/mmol Cr). CTX-II levels in urine were evaluated using a commercial enzyme-linked immunosorbent assay (ELISA) from Immunodiagnostics Systems, Inc. (Urine CartiLaps® EIA) according to manufacturer instructions. Baseline urine samples were collected from the $2^{nd}$ void of the morning and were frozen (−20° C.) immediately and held until needed for assaying. When samples were thawed, they were subdivided into aliquots to avoid subsequent repeated freeze/thaw cycles that might result in aberrant repeat assay values.

Two females (ages 34 & 37) and one male (age 34) all with a BMI <25 kg/m$^2$ and having healthy knee joints provided baseline urine samples for basal CTX-II level determination. The subjects subsequently performed exercises (females: 300 stairs per leg over 10-15 minutes; male: jogged 4 miles over ~45 minutes) that would be expected to increase levels of excreted urinary CTX-II. Subjects provided urine samples approximately every 2-4 hours to follow CTX-II clearance temporally (over time) to determine when the maximum post-exercise CTX-II level would be observed.

Similarly, a post-menopausal female (age 60) with a BMI <25 kg/m$^2$ and diagnosed osteoarthritis of the right knee provided a baseline urine sample for basal CTX-II level determination. The subject subsequently performed exercise (300 stairs per leg over 10-15 minutes) that would be expected to increase levels of excreted urinary CTX-II. The subject provided urine samples approximately every 2-4 hours to follow CTX-II clearance temporally (over time) to determine when the maximum post-exercise CTX-II level would be observed. The results of the clearance evaluations are graphed in FIG. 1.

Figure 1:
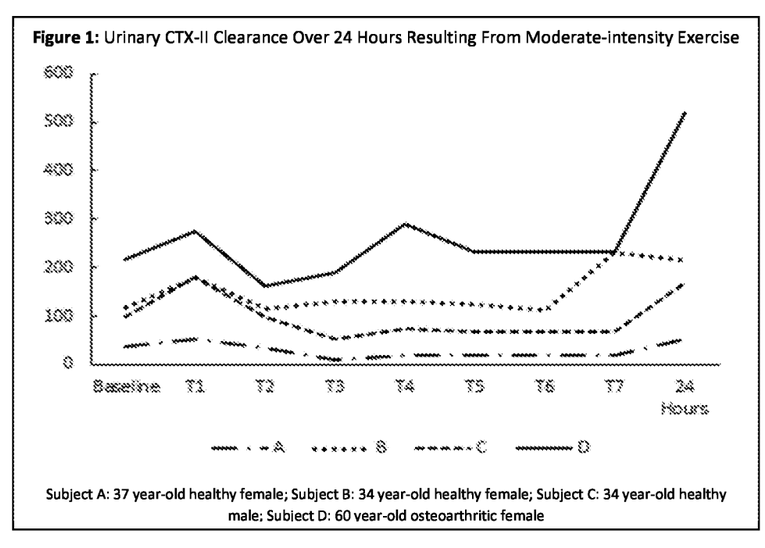
FIG. 1: Urinary CTX-II clearance over 24 hours resulting from moderate-intensity exercise.

There is a reliable increase in CTX-II within the first urine sample following exercise (2-4 hours), however the most consistent and generally largest increase is noted at 24 hours post-exercise ($2^{nd}$ void). For Subject A (37 year-old healthy female; 300 stairs per leg), the increase from baseline to 24-hours was 37.6%. For Subject B (34 year-old healthy female; 300 stairs per leg), the increase from baseline to 24-hours was 85.5%. For Subject C (34 year-old healthy male; jogged 4 miles), the increase from baseline to 24-hours was 69.9%. For Subject D (60 year-old post-menopausal arthritic female; 300 stairs per leg), the increase from baseline to 24-hours was 139.7%. The post-menopausal arthritic subject (D) had an increase anywhere from 1.5-fold (Subject B) to 3.5-fold (Subject A) that of younger pre-menopausal females with healthy knee joints.

Example 2

Increase of the Cartilage Degradation Biomarker CTX-II in Urine in an Arthritic, Post-menopausal Human Female Resulting from a Low-impact, Moderate-intensity Exercise Regimen The following example is illustrative of the increase of the cartilage degradation biomarker CTX-II in urine in an arthritic, post-menopausal human female resulting from a low-impact, moderate-intensity exercise regimen. CTX-II levels are reported as in Example 1 and were determined from the $2^{nd}$ void of the morning collected within 12-24 hours after completing the last exercise. A post-menopausal female (age 58) with diagnosed osteoarthritis of the left knee who exercised fewer than 2 times per week provided a baseline urine sample for basal CTX-II level determination (119 ng/mmole Cr). The subject subsequently performed exercise for 7-10 minutes on alternating days for two consecutive weeks on a seated step machine (NuStep® brand) with a workload of 5.0 and a pace of approximately 70 steps per minute. At the end of each week, the subject provided a urine sample for the comparison of CTX-II levels to baseline. At week 1, CTX-II had increased by 77.9% (211 ng/mmole Cr) from baseline and at week 2, CTX-II was similarly increased by 75.3% (208 ng/mmole Cr) from baseline.

Example 3

Increase of the Cartilage Degradation Biomarker CTX-II in Urine in a Healthy, Post-menopausal Human Female Resulting from a Low-impact, Moderate-intensity Exercise Regimen The following example is illustrative of the increase of the cartilage degradation biomarker CTX-II in urine in a healthy, post-menopausal human female resulting from a low-impact, moderate-intensity exercise regimen. CTX-II levels are reported as in Example 1 and were determined from the $2^{nd}$ void of the morning collected within 12-24 hours after completing the last exercise. A post-menopausal female (age 67) with healthy knee joints (no knee pain or stiffness) who exercised fewer than 2 times per week provided a baseline urine sample for basal CTX-II level determination (156 ng/mmole Cr). The subject subsequently performed exercise for 7-10 minutes on alternating days for two consecutive weeks on an inclined treadmill with an incline of 14 degrees and a pace of 1.7 miles per hour. At the end of each week, the subject provided a urine sample for the comparison of CTX-II levels to baseline. At week 1, CTX-II had increased by 20.4% (188 ng/mmole Cr) from baseline and at week 2, CTX-II was similarly increased by 27.1% (199 ng/mmole Cr) from baseline.

Example 4

Increase of the Cartilage Degradation Biomarker CTX-II in Urine in a Healthy, Obese Human Male Resulting from a Low-impact, Moderate-intensity Exercise Regimen The following example is illustrative of the increase of the cartilage degradation biomarker CTX-II in urine in a healthy, obese human male resulting from a low-impact, moderate-intensity exercise regimen. CTX-II levels are reported as in Example 1 and were determined from the $2^{nd}$ void of the morning collected within 12-24 hours after completing the last exercise. An obese male (age 43) with BMI >25 kg/m$^2$ and having healthy knee joints (no knee pain or stiffness) who exercised fewer than 2 times per week provided a baseline urine sample for basal CTX-II level determination (70 ng/mmole Cr). The subject subsequently performed exercise of 50 stairs (standard height) per leg over approximately 10 minutes daily for one week. On Day 4 and Day 8, the subject provided a urine sample for the comparison of CTX-II levels to baseline. On Day 4, CTX-II had increased by 43.6% (100 ng/mmole Cr) from baseline and on Day 8, CTX-II was increased by 24.3% (87 ng/mmole Cr) from baseline.

Example 5

Comparison of the Increase of the Cartilage Degradation Biomarker CTX-II in Urine in a Group of Healthy, Post-menopausal Human Females Resulting from Three Different Low-impact, Moderate-intensity Exercise Regimens The following example is illustrative of the comparison of the increase of the cartilage degradation biomarker CTX-II in urine in a group of healthy, post-menopausal human females resulting from three different low-impact, moderate-intensity exercise regimens. CTX-II levels are reported as in Example 1 and were determined from the $2^{nd}$ void of the morning collected within 12-24 hours after completing the last exercise. The study described below was conducted in accordance with the U.S. Food & Drug Administration's principles of Good Clinical Practice (Title 21, Code of Federal Regulations, Parts 50 & 56 and ICH E6) and the Declaration of Helsinki. The study protocol was approved by a duly authorized Institutional Review Board (IRB) and all subjects provided their written informed consent in order to participate.

A group of 30 post-menopausal females (age range 46-72) with healthy knee joints (no knee pain or stiffness) all of whom exercised fewer than 2 times per week were randomized into one of three different low-impact, moderate-intensity exercise regimen groups. Group A subjects walked for a minimum of 7 minutes on alternating days for two consecutive weeks on a 14 degree inclined treadmill at a pace of 1.7 miles per hour. Group B subjects performed exercise for a minimum of 7 minutes on alternating days for two consecutive weeks on a seated step machine (NuStep® brand) with a workload of 7.0 and a pace of 30-40 steps per minute. Group C subjects performed 3 sets of 8 lifts each of 90 pounds (41 kg) on a seated leg press (Cybex® brand) in a maximum of 7 minutes on alternating days for two consecutive weeks. All subjects provided baseline urine samples for basal CTX-II level determination and urine samples at the end of each week for the comparison of CTX-II levels to baseline. Table 2 contains the baseline demographic data for the three groups of study subjects.

TABLE 2

| Subject Baseline Demographics | | | |
|---|---|---|---|
| | Group A | Group B | Group C |
| Age, yrs | 58.2 ± 4.7 | 52.4 ± 6.2 | 57.8 ± 7.1 |
| Weight, kg | 73.4± | 83.5± | 77.2± |
| BMI | 26.8 ± 3.4 | 30.1 ± 4.4 | 28.6 ± 4.2 |
| uCTX-II (ng/mmole | 259 ± 102 | 219 ± 98 | 288 ± 84 |

Values are reported as mean ± standard deviation (SD) (n = 30).
BMI was determined as weight in kilograms The three groups were not statistically different in any of the baseline demographic data using the non-parametric Kruskal-Wallis Test for multiple groups. It is also significant that their urinary CTX-II levels are consistent with being healthy post-menopausal females, having average CTX-II levels at the very lowest end of the range of what would be expected for arthritic subjects and well within the expected normal range for women of their age and hormonal status (see supra Table 1). Table 3 shows the urinary CTX-II results for the three groups of subjects after preforming the designated exercise regimens for two consecutive weeks.

TABLE 3

Urinary CTX-II levels at Baseline and after 1 Week & 2 Weeks of performing one of three low-impact, moderate-intensity exercise regimens.

| | Time Point | uCTX-II | % Difference -vs- Baseline |
|---|---|---|---|
| Group A | Baseline | 259 ± 102 | N/A |
| | Week 1 | 223 ± 80 | −14.0 |
| | Week 2 | 228 ± 88 | −11.6 |
| Group B | Baseline | 219 ± 98 | N/A |
| | Week 1 | 233 ± 103 | +6.4 |
| | Week 2 | 218 ± 102 | −0.5 |
| Group C | Baseline | 288 ± 84 | N/A |
| | Week 1 | 331 ± 117 | +14.9 |
| | Week 2 | 313 ± 108 | +8.7 |

Values are reported as mean ± standard deviation (SD) (n = 10 per group).

Using the non-parametric Friedman Test for repeated measures coupled with a post-hoc Conover analysis to determine which time points (Baseline, Week 1, or Week 2) differed, it was determined that Group C differed statistically (P<0.05) from Baseline at both Week 1 & Week 2. Group A showed a clear statistical trend (P<0.10) for Week 1 & Week 2 to differ from Baseline. Group B was not statistically different at any time point. When reviewing the data across all groups, there is a clear trend for the strenuous nature (lifting weight>seated step machine>inclined treadmill) of the exercise to affect the magnitude of the cartilage turnover of the knee joint. This unexpected finding compared to the known effect from the nature of the impact (low- versus high-) of the exercise on the joint enables the evaluation of exercise induced cartilage turnover.

Only one or two subjects in Group A experienced any pain or stiffness from walking on an inclined treadmill (as described previously). Therefore the pain & stiffness results for Group B & Group C only are reported in Table 4.

TABLE 4

Pain & Stiffness levels at Baseline and after 1 Week & 2 Weeks of performing one of two low-impact, moderate-intensity exercise regimens.

|  | Time Point | Immediate Pain (% increase) | 12-hour Pain (% increase) | Immediate Stiffness (% increase) | 12-hour Stiffness (% increase) |
|---|---|---|---|---|---|
| Group B | Baseline | 0.1 ± 0.3 (N/A) | 0.1 ± 0.3 (N/A) | 0.2 ± 0.4 (N/A) | 0.2 ± 0.4 (N/A) |
|  | Week 1 | 0.6 ± 1.0 (500%)† | 0.7 ± 1.1 (600%)* | 0.9 ± 1.0 (350%)† | 0.9 ± 1.0 (350%)† |
|  | Week 2 | 0.8 ± 1.5 (700%)† | 0.8 ± 1.1 (700%)* | 0.6 ± 1.1 (200%) | 0.9 ± 1.1 (350%)† |
| Group C | Baseline | 0.1 ± 0.3 (N/A) | 0.1 ± 0.3 (N/A) | 0.3 ± 0.5 (N/A) | 0.3 ± 0.5 (N/A) |
|  | Week 1 | 1.0 ± 0.8 (900%)* | 1.0 ± 1.1 (900%)* | 1.0 ± 0.8 (233%)* | 1.2 ± 1.0 (300%)* |
|  | Week 2 | 0.8 ± 0.8 (700%)* | 0.7 ± 1.1 (600%)† | 1.2 ± 1.0 (300%)* | 0.9 ± 1.1 (233%)† |

Values are reported as mean ± standard deviation (SD) (n = 10 per group).
% increase is versus baseline.
*= P < 0.05;
†= P ~0.10

There were substantial increases in pain in both groups, both immediately after exercise (500-900%) and after 12 hours post-exercise (600-900%). Similarly, there were substantial increases in stiffness in both groups, both immediately after exercise (200-350%) and after 12 hours post-exercise (233-350%). For Group B, these results were statistically significant (P<0.05) for 12-hour post-exercise pain (Week 1 & Week 2) and showed a statistical trend (P~0.10) for immediate pain (both weeks), immediate stiffness (Week 1), and 12-hour post-exercise stiffness (both weeks). For Group C, these results were statistically significant (P<0.05) for all categories (immediate pain & stiffness and 12-hour post-exercise pain & stiffness) at Week 1 and for Week 2 immediate pain & stiffness and showed a statistical trend (P~0.10) for Week 2 12-hour post-exercise pain & stiffness.

Example 6

Open-Label Evaluation of a Joint Therapeutic Composition Via the Urinary Cartilage Degradation Biomarker CTX-II in a Group of Healthy, Post-menopausal Human Females Resulting from a Single Low-impact, Moderate-intensity Exercise Regimen The following example is illustrative of the open-label evaluation of a joint therapeutic composition via the urinary cartilage degradation biomarker CTX-II in a group of healthy, post-menopausal human females resulting from a single low-impact, moderate-intensity exercise regimen. CTX-II levels are reported as in Example 1 and were determined from the $2^{nd}$ void of the morning collected within 12-24 hours after completing the last exercise. The study described below was conducted in accordance with the U.S. Food & Drug Administration's principles of Good Clinical Practice (Title 21, Code of Federal Regulations, Parts 50 & 56 and ICH E6) and the Declaration of Helsinki. The study protocol was approved by a duly authorized Institutional Review Board (IRB) and all subjects provided their written informed consent in order to participate.

The same group (from Example 5) of 30 post-menopausal females (age range 46-72) with healthy knee joints (no knee pain or stiffness) all of whom exercised fewer than 2 times per week were re-randomized into one of two different treatment groups (following a 3 week resting period). All subjects performed the same low-impact, moderate-intensity exercise regimen (3 sets of 8 lifts each of 90 pounds (41 kg) on a seated leg press (Cybex® brand) in a maximum of 7 minutes on alternating days for two consecutive weeks). Group 1 subjects consumed one 500 mg capsule per day of a powdered eggshell membrane joint therapeutic composition (commercially available as NEM® brand eggshell membrane) for 7 days prior to beginning the exercise regimen and continued to take the treatment during the two-week exercise period (3 weeks total). Group 2 subjects consumed one 500 mg capsule per day of the same powdered eggshell membrane joint therapeutic composition, but began taking it on Day 1 of the two-week exercise period and continued to do so throughout the remaining time (2 weeks total). All subjects provided baseline urine samples for basal CTX-II level determination and urine samples at the end of each week for the comparison of CTX-II levels to baseline. Table 5 contains the baseline demographic data for the two groups of study subjects.

TABLE 5

Subject Baseline Demographics

|  | Group 1 | Group 2 |
|---|---|---|
| Age, yrs | 56.2 ± 8.0 | 56.1 ± 4.8 |
| Weight, kg | 78.4± | 77.7± |
| BMI | 28.4 ± 3.7 | 28.6 ± 4.7 |
| uCTX-II (ng/mmole | 220 ± 97 | 174 ± 76 |

Values are reported as mean ± standard deviation (SD) (n = 30).
BMI was determined as weight in kilograms divided by height in meters squared.

The groups were not statistically different in any of the baseline demographic data using the non-parametric Mann-Whitney U Test for independent groups. It is also significant that their urinary CTX-II levels had returned to levels similar to what was found in Example 5 following the 3-week resting period. Again, CTX-II levels are consistent with being healthy post-menopausal females, having average CTX-II levels at the very lowest end of the range of what would be expected for arthritic subjects and well within the expected normal range for women of their age and hormonal status (see supra Table 1). Table 6 shows the urinary CTX-II results for the two groups of subjects after preforming the designated exercise regimen for two consecutive weeks.

TABLE 6

Urinary CTX-II levels at Baseline and after 1 Week & 2 Weeks of performing a low-impact, moderate-intensity exercise regimen while consuming a joint therapeutic composition.

|  | Time Point | uCTX-II | % Difference -vs- Baseline |
|---|---|---|---|
| Group 1 | Baseline | 220 ± 97 | N/A |
|  | Week 1 | 222 ± 92 | +1.3 |
|  | Week 2 | 209 ± 93 | −4.8 |
| Group 2 | Baseline | 174 ± 76 | N/A |
|  | Week 1 | 178 ± 87 | +2.3 |
|  | Week 2 | 161 ± 58 | −5.7 |

Values are reported as mean ± standard deviation (SD) (n = 15 per group).

There were no statistical differences for either group from baseline for urinary CTX-II, which is in contrast to the results found in Group C in Example 5 (performing the same exercise regimen), indicating that the NEM® brand eggshell membrane joint therapeutic composition is chondroprotective (cartilage-sparing) in this clinical trial designed to induce cartilage turnover via exercise. Because there were also no statistically significant differences between Group 1 & Group 2 for any of the pain or stiffness categories (see Table 7 for a summary), the same 10 subjects from Group C, Example 5 were compared directly to their results obtained in Example 5 from performing the same exercise regimen when not consuming a joint therapeutic composition (see Table 8 for a summary).

TABLE 7

Pain & Stiffness levels at Baseline and after 1 Week & 2 Weeks of performing a low-impact, moderate-intensity exercise regimen while consuming a joint therapeutic composition.

|  | Time Point | Immediate Pain (% increase) | 12-hour Pain (% increase) | Immediate Stiffness (% increase) | 12-hour Stiffness (% increase) |
|---|---|---|---|---|---|
| Group 1 | Baseline | 0.4 ± 1.1 (N/A) | 0.4 ± 1.1 (N/A) | 0.5 ± 1.0 (N/A) | 0.5 ± 1.0 (N/A) |
|  | Week 1 | 1.2 ± 1.9 (200%) | 1.1 ± 1.7 (168%) | 0.8 ± 1.3 (50%) | 1.0 ± 1.7 (88%) |
|  | Week 2 | 0.7 ± 1.4 (83%) | 0.6 ± 1.0 (50%) | 0.7 ± 1.2 (25%) | 0.7 ± 1.0 (25%) |
| Group 2 | Baseline | 0.4 ± 0.7 (N/A) | 0.4 ± 0.7 (N/A) | 0.6 ± 1.0 (N/A) | 0.6 ± 1.0 (N/A) |
|  | Week 1 | 0.9 ± 0.8 (117%) | 0.7 ± 0.9 (83%) | 0.9 ± 0.9 (44%) | 0.8 ± 1.1 (33%) |
|  | Week 2 | 0.9 ± 0.7 (117%) | 0.3 ± 0.6 (−17%) | 0.6 ± 0.6 (0%) | 0.5 ± 0.7 (−11%) |

Values are reported as mean ± standard deviation (SD) (n = 15 per group).
% increase is versus baseline.

TABLE 8

Urinary CTX-II, Pain, and Stiffness levels at Baseline and after 1 Week & 2 Weeks of performing a low-impact, moderate-intensity exercise regimen while both untreated and while consuming a joint therapeutic composition.

|  | Weeks Post-treatment | Treatment Untreated | Treatment NEM® | Absolute Treatment Effect |
|---|---|---|---|---|
| uCTX-II | Baseline (n = 10, 10) | 288 ± 84 | 237 ± 82 | N/A |
|  | 1 (n = 10, 10) | 331 ± 117 | 227 ± 85 | −19.1% |
|  | 2 (n = 10, 10) | 313 ± 108 | 230 ± 70 | −11.7%† |
| Immediate Pain | Baseline (n = 10, 10) | 0.1 ± 0.3 | 0.6 ± 1.0 | N/A |
|  | 1 (n = 10, 10) | 1.0 ± 0.8 | 0.8 ± 0.9 | −867%† |
|  | 2 (n = 10, 10) | 0.8 ± 0.8 | 0.7 ± 0.8 | −683%† |
| 12-hour Pain | Baseline (n = 10, 10) | 0.1 ± 0.3 | 0.6 ± 1.0 | N/A |
|  | 1 (n = 10, 10) | 1.0 ± 1.1 | 0.7 ± 0.9 | −883%* |
|  | 2 (n = 10, 10) | 0.7 ± 1.1 | 0.4 ± 0.7 | −633%† |
| Immediate Stiffness | Baseline (n = 10, 10) | 0.3 ± 0.5 | 0.8 ± 1.1 | N/A |
|  | 1 (n = 10, 10) | 1.0 ± 0.8 | 0.9 ± 1.1 | −220%† |
|  | 2 (n = 10, 10) | 1.2 ± 1.0 | 0.6 ± 0.8 | −325%* |
| 12-hour Stiffness | Baseline (n = 10, 10) | 0.3 ± 0.5 | 0.8 ± 1.1 | N/A |
|  | 1 (n = 10, 10) | 1.2 ± 1.0 | 0.9 ± 1.3 | −287%† |
|  | 2 (n = 10, 10) | 0.9 ± 1.1 | 0.6 ± 0.8 | −258%* |

Except where indicated otherwise, values are reported as mean ± standard deviation (SD).
Absolute Treatment Effect is the net difference of NEM treatment versus untreated for the change in mean treatment effect from baseline expressed as a percent.
Negative values for pain or function indicate superior improvement in the treatment group.
*P < 0.05;
†P < 0.10

Example 7

Randomized, Double-Blind, Placebo-Controlled Evaluation of a Joint Therapeutic Composition Via the Urinary Cartilage Degradation Biomarker CTX-II in a Group of Healthy, Post-menopausal Human Females Resulting from a Single Low-impact, Moderate-intensity Exercise Regimen The following example is illustrative of the randomized, double-blind, placebo-controlled evaluation of a joint therapeutic composition via the urinary cartilage degradation biomarker CTX-II in a group of healthy, post-menopausal human females resulting from a single low-impact, moderate-intensity exercise regimen. CTX-II levels are reported as in Example 1 and were determined from the $2^{nd}$ void of the morning collected within 12-24 hours after completing the last exercise. The study described below was conducted in accordance with the U.S. Food & Drug Administration's principles of Good Clinical Practice (Title 21, Code of Federal Regulations, Parts 50 & 56 and ICH E6) and the Declaration of Helsinki. The study protocol was approved by a duly authorized Institutional Review Board (IRB) and all subjects provided their written informed consent in order to participate.

A group of 60 post-menopausal females (age range 44-71) with healthy knee joints (no knee pain or stiffness) all of whom exercised fewer than 2 times per week were randomized into one of two blinded treatment groups (either 500 mg of NEM® brand eggshell membrane or 500 mg of placebo, daily). All subjects performed the same low-impact, moderate-intensity exercise regimen (50-100 steps per leg in less than 10 minutes on alternating days for two consecutive weeks). The number of steps each participant would perform was determined at screening and the participant performed this set number of steps throughout the trial. All subjects provided baseline urine samples for basal CTX-II level determination and urine samples at the end of each week for the comparison of CTX-II levels between the treatment groups (i.e. therapeutic versus placebo). Table 9 contains the baseline demographic data for the two groups of study subjects.

TABLE 9

Subject Baseline Demographics

|  | NEM | Placebo |
|---|---|---|
| Age, yrs | 56.1 ± 7.4 | 57.7 ± 7.9 |
| Weight, kg | 75.7± | 78.1± |
| BMI | 28.2 ± 5.4 | 28.8 ± 4.4 |
| uCTX-II (ng/mmole | 258 ± 105 | 236 ± 175 |

Values are reported as mean ± standard deviation (SD) (n = 60).
BMI was determined as weight in kilograms divided by height in meters squared.

The groups were not statistically different in any of the baseline demographic data using the parametric Student's t Test for independent groups. Again, CTX-II levels are consistent with being healthy post-menopausal females, having average CTX-II levels at the very lowest end of the range of what would be expected for arthritic subjects and well within the expected normal range for women of their age and hormonal status (see supra Table 1). Table 10 shows the urinary CTX-II results for the two groups of subjects after preforming the designated exercise regimen for two consecutive weeks.

TABLE 10

Urinary CTX-II, Pain, and Stiffness levels at Baseline and after 1 Week & 2 Weeks of performing a low-impact, moderate-intensity exercise regimen while consuming either a joint therapeutic composition or a placebo.

|  | Weeks Post-treatment | Treatment NEM ® | Treatment Placebo | Absolute Treatment Effect |
|---|---|---|---|---|
| uCTX-II | Baseline (n = 31, 29) | 258 ± 105 | 236 ± 175 | N/A |
|  | 1 (n = 31, 29) | 234 ± 83 | 255 ± 172 | −17.2%** |
|  | 2 (n = 31, 29) | 242 ± 101 | 245 ± 184 | −9.9%* |
| Immediate Pain | Baseline (n = 31, 29) | 1.4 ± 1.1 | 1.4 ± 1.4 | N/A |
|  | 1 (n = 31, 29) | 1.2 ± 1.2 | 1.6 ± 1.5 | −28.6% |
|  | 2 (n = 31, 29) | 0.7 ± 0.9 | 1.3 ± 1.5 | −42.9%† |
| 12-hour Pain | Baseline (n = 31, 29) | 0.2 ± 0.4 | 0.5 ± 0.8 | N/A |
|  | 1 (n = 31, 29) | 0.4 ± 0.6 | 1.0 ± 1.3 | 0% |
|  | 2 (n = 31, 29) | 0.3 ± 0.6 | 0.8 ± 1.2 | −10%* |
| Immediate Stiffness | Baseline (n = 31, 29) | 1.3 ± 1.0 | 1.7 ± 1.3 | N/A |
|  | 1 (n = 31, 29) | 0.9 ± 0.9 | 1.7 ± 1.5 | −30.8%* |
|  | 2 (n = 31, 29) | 0.7 ± 0.9 | 1.2 ± 1.5 | −16.7%† |
| 12-hour Stiffness | Baseline (n = 31, 29) | 0.3 ± 0.6 | 0.6 ± 0.9 | N/A |
|  | 1 (n = 31, 29) | 0.5 ± 0.7 | 1.0 ± 1.2 | 0% |
|  | 2 (n = 31, 29) | 0.3 ± 0.6 | 0.9 ± 1.4 | −33.3%* |

Figure 2:
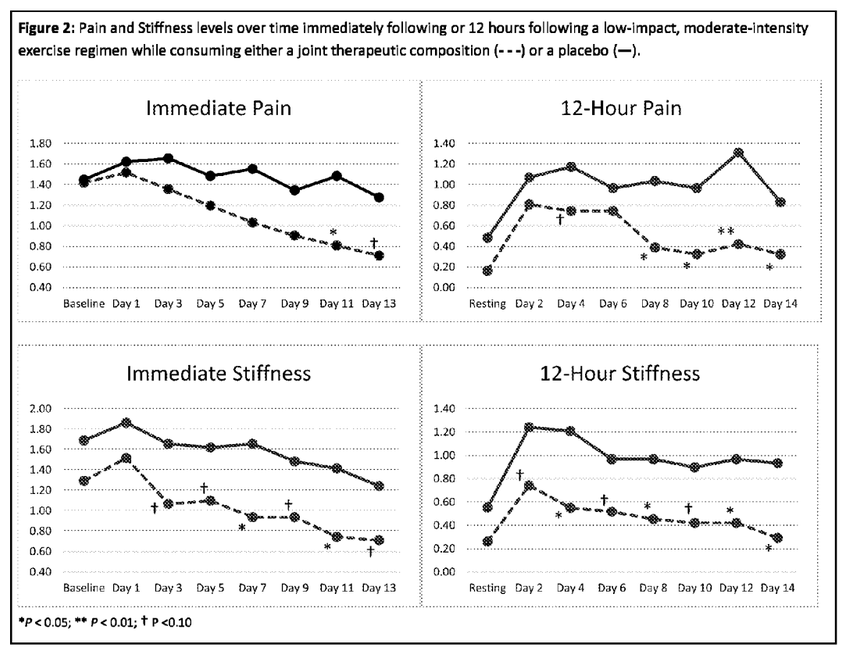
FIG. 2: Pain and stiffness levels over time immediately following or 12 hours following a low impact, moderate intensity exercise regimen while consuming either a joint therapeutic composition or a placebo.

Except where indicated otherwise, values are reported as mean ± standard deviation (SD).
Absolute Treatment Effect is the net difference of NEM treatment versus placebo for the change in mean treatment effect from baseline expressed as a percent.
Negative values for pain or function indicate superior improvement in the treatment group.
*$P < 0.05$;
**$P < 0.01$;
†$P < 0.10$ The NEM-treated group showed statistically significant reductions in CTX-II versus placebo at both Week 1 and Week 2, again indicating that the NEM® brand eggshell membrane joint therapeutic composition is chondroprotective (cartilage-sparing) in this clinical trial designed to induce cartilage turnover via exercise. The NEM-treated group also showed statistically significant reductions in stiffness immediately following exercise on Days 7 & 11, and for 12-hour post-exercise pain and stiffness on Days 8-14 & 4, 8, 12, & 14, respectively (see FIG. 2). This demonstrates that the NEM® brand eggshell membrane joint therapeutic composition also reduces the symptomology (i.e. pain & stiffness) resulting from exercise and aids in recovery from exercise.

What is claimed is:

1. A method for determining the efficacy of a composition used to treat articular joint conditions in mammals, wherein the method comprises
   i. measuring the change in levels of c-terminal cross-linked telopeptide of type-II collagen (CTX-II) in said mammal from before exercise and after exercise, wherein the exercise is performed for a brief period per day for a duration of from 24 hours to 4 weeks; and wherein the exercise is of low impact to the articular joint and of moderate intensity;
   ii. subsequently administering a composition used to treat articular joint conditions to said mammal; and
   iii. subsequently measuring the change in levels of CTX-II in said mammal from before exercise and after exercise, wherein a decrease in the change in levels of CTX-II after exercise in step (iii) as compared to the level of said CTX II after exercise in step (i) indicates that said composition is effective to treat articular joint conditions in said mammal.

2. A method for determining the efficacy of a composition used to treat articular joint conditions in mammals, wherein the method comprises
   i. administering a composition used to treat articular joint conditions to all but one group of two or more groups of mammals; and
   ii. subsequently measuring the change in levels of c-terminal cross-linked telopeptide of type-II collagen (CTX-II) in said groups of mammals from before exercise and after exercise, wherein the exercise is performed for a brief period per day for a duration of from 24 hours to 4 weeks; and
   wherein the exercise is of low impact to the articular joint and of moderate intensity;
   wherein a decrease in the change in levels of CTX-II after exercise in step (ii) for the group or groups administered a composition in step (i) as compared to the change in levels of said CTX-II after exercise in step (ii) for the group that was not administered a composition in step (i) indicates that said composition is effective to treat articular joint conditions in said mammals.

3. The method according to claim 1, wherein the cartilage degradation biomarkers are obtained from synovial fluid, whole blood, serum, or urine of said mammal.

4. The method according to claim 1, wherein the articular joint is selected from the group consisting of spine, shoulders, elbows, wrists, fingers, hips, knees, ankles, and toes.

5. The method according to claim 1, wherein the exercise is selected from the group consisting of walking, roller skating, swimming, cycling, yoga, rowing, water aerobics, stair climbing, and weight lifting.

6. The method according to claim 1, wherein the mammal is suffering from an articular joint disease.

7. The method according to claim 6, wherein the articular joint disease is selected from the group consisting of osteoarthritis, rheumatoid arthritis, psoriatic arthritis, juvenile arthritis, ankylosing spondylitis, gout, gouty arthritis, tendinitis, synovitis, Sjögren's Syndrome, septic arthritis, or systemic lupus erythematosis.

8. The method according to claim 1, where the mammal is pre-diseased, or is completely asymptomatic, but has underlying detrimental articular joint structural changes.

9. The method according to claim 8, where the mammal is obese or a post-menopausal female, or a combination thereof.

10. The method according to claim 1, where the mammal is healthy and does not experience any articular joint disease symptoms nor has any underlying detrimental articular joint structural changes.

11. The method according to claim 10, where the mammal is obese or a post-menopausal female, or a combination thereof.

12. The method according to claim 1, wherein the composition is a chondroprotective agent.

13. The method according to claim 12, where the chondroprotective agent is selected from the group consisting of glucosamine; glycosaminoglycans; chondroitin sulfate; methylsulfonylmethane (MSM); S-adenosylmethionine (SAMe); eggshell membrane or eggshell membrane hydrolysates; an omega-3 or omega-6 polyunsaturated fatty acid; *Boswellia* species or *Boswellia* extract; turmeric or turmeric extract; curcumin or curcuminoids; white willow bark or white willow bark extract; proteolytic enzymes; collagen or collagen hydrolyzates; pine bark extract; cetylated fatty acids; plant extracts; a vitamin or vitamin pre-cursor; a mineral, or combinations thereof.

14. The method according to claim 1, wherein the composition affects or is intended to affect joint-related symptomology.

15. The method according to claim 14, wherein joint-related symptomology is selected from the group consisting of pain; burning; aching; tenderness; discomfort; stiffness; swelling; localized fever or warmth; inflexibility; limitation in or decreased range of motion; crepitus; partial loss of function; loss of weight-bearing capacity or weakness; or combinations thereof.

16. The method according to claim 14, where the joint-related symptomology is evaluated during or immediately after exercise or some time period following exercise, or a combination thereof.

17. The method according to claim 2, wherein the cartilage degradation biomarkers are obtained from synovial fluid, whole blood, serum, or urine of said mammal.

18. The method according to claim 2, wherein the articular joint is selected from the group consisting of spine, shoulders, elbows, wrists, fingers, hips, knees, ankles, and toes.

19. The method according to claim 2, wherein the exercise is selected from the group consisting of walking, roller skating, swimming, cycling, yoga, rowing, water aerobics, stair climbing, and weight lifting.

20. The method according to claim 2, wherein the mammal is suffering from an articular joint disease.

21. The method according to claim 2, wherein the articular joint disease is selected from the group consisting of osteoarthritis, rheumatoid arthritis, psoriatic arthritis, juvenile arthritis, ankylosing spondylitis, gout, gouty arthritis, tendinitis, synovitis, Sjögren's Syndrome, septic arthritis, or systemic lupus erythematosis.

22. The method according to claim 2, where the mammal is pre-diseased, or is completely asymptomatic, but has underlying detrimental articular joint structural changes.

23. The method according to claim 2, where the mammal is obese or a post-menopausa female, or a combination thereof.

24. The method according to claim 2, where the mammal is healthy and does not experience any articular joint disease symptoms nor has any underlying detrimental articular joint structural changes.

25. The method according to claim 24, where the mammal is obese or a post-menopausal female, or a combination thereof.

26. The method according to claim 2, wherein the composition is a chondroprotective agent.

27. The method according to claim 26, where the chondroprotective agent is selected from the group consisting of glucosamine; glycosaminoglycans; chondroitin sulfate; methylsulfonylmethane (MSM); S-adenosylmethionine (SAMe); eggshell membrane or eggshell membrane hydrolysates; an omega-3 or omega-6 polyunsaturated fatty acid; *Boswellia* species or *Boswellia* extract; turmeric or turmeric extract; curcumin or curcuminoids; white willow bark or white willow bark extract; proteolytic enzymes; collagen or collagen hydrolyzates; pine bark extract; cetylated fatty acids; plant extracts; a vitamin or vitamin pre-cursor; a mineral, or combinations thereof.

28. The method according to claim 2, wherein the composition affects or is intended to affect joint-related symptomology.

29. The method according to claim 28, wherein joint-related symptomology is selected from the group consisting of pain; burning; aching; tenderness; discomfort; stiffness; swelling; localized fever or warmth; inflexibility; limitation in or decreased range of motion; crepitus; partial loss of function; loss of weight-bearing capacity or weakness; or combinations thereof.

30. The method according to claim 28, where the joint-related symptomology is evaluated during or immediately after exercise or some time period following exercise, or a combination thereof.

* * * * *

UNITED STATES PATENT AND TRADEMARK OFFICE
CERTIFICATE OF CORRECTION

PATENT NO.         : 9,983,214 B2
APPLICATION NO.    : 15/130120
DATED              : May 29, 2018
INVENTOR(S)        : Kevin J. Ruff Page 1 of 1

It is certified that error appears in the above-identified patent and that said Letters Patent is hereby corrected as shown below:

In the Claims

Column 22, Line 16 Claim 23:
Now reads: "post-menopausa female,"
Should read: --post-menopausal female,--.

Signed and Sealed this
Fourteenth Day of August, 2018

Andrei Iancu
*Director of the United States Patent and Trademark Office*